United States Patent
Solem et al.

(10) Patent No.: US 7,311,728 B2
(45) Date of Patent: *Dec. 25, 2007

(54) DEVICE AND METHOD FOR TREATMENT OF MITRAL INSUFFICIENCY

(75) Inventors: Jan Otto Solem, Stetten (CH); Per Ola Kimblad, Lund (SE)

(73) Assignee: Edwards Lifesciences AG, Saint-Prex (CH)

( * ) Notice: Subject to any disclaimer, the term of this patent is extended or adjusted under 35 U.S.C. 154(b) by 474 days.

This patent is subject to a terminal disclaimer.

(21) Appl. No.: 10/953,047

(22) Filed: Sep. 29, 2004

(65) Prior Publication Data

US 2005/0043792 A1 Feb. 24, 2005

Related U.S. Application Data

(63) Continuation of application No. 10/019,563, filed as application No. PCT/SE00/01369 on Jun. 28, 2000, now Pat. No. 7,044,967.

(30) Foreign Application Priority Data

Jun. 29, 1999 (SE) .................................. 9902455

(51) Int. Cl.
*A61F 2/06* (2006.01)
(52) U.S. Cl. .................................... 623/2.36
(58) Field of Classification Search ....... 623/2.36–2.37
See application file for complete search history.

(56) References Cited

U.S. PATENT DOCUMENTS 4,164,046 A    8/1979    Cooley
4,655,771 A    4/1987    Wallsten
4,954,126 A    9/1990    Wallsten
5,006,106 A    4/1991    Angelchik
5,061,275 A    10/1991   Wallsten et al.
5,064,435 A    11/1991   Porter
5,071,407 A    12/1991   Termin et al.
5,104,404 A    4/1992    Wolff (Continued)

FOREIGN PATENT DOCUMENTS

DE    196 05 042 A1    1/1998
DE    196 11 755 A1    2/1998
EP    0 727 239 A2     8/1996

(Continued)

OTHER PUBLICATIONS

Laaksovirta et al., *Expansion and bioabsorption of the self-reinforced lactic and glycolic acid copolymer prostatic spiral stent*, PubMed, Excerpt from J Urol Sep. 2001; 166(3):919-22, one sheet.

(Continued)

*Primary Examiner*—Suzette Gherbi
(74) *Attorney, Agent, or Firm*—David L. Hauser; Christie Parker & Hale

(57) ABSTRACT

A device for treatment of mitral annulus dilatation comprises an elongate body having two states. In a first of these states the elongate body is insertable into the coronary sinus and has a shape adapting to the shape of the coronary sinus. When positioned in the coronary sinus, the elongate body is transferable to the second state assuming a reduced radius of curvature, whereby the radius of curvature of the coronary sinus and the radius of curvature as well as the circumference of the mitral annulus is reduced.

25 Claims, 5 Drawing Sheets

U.S. PATENT DOCUMENTS

Figure 1:
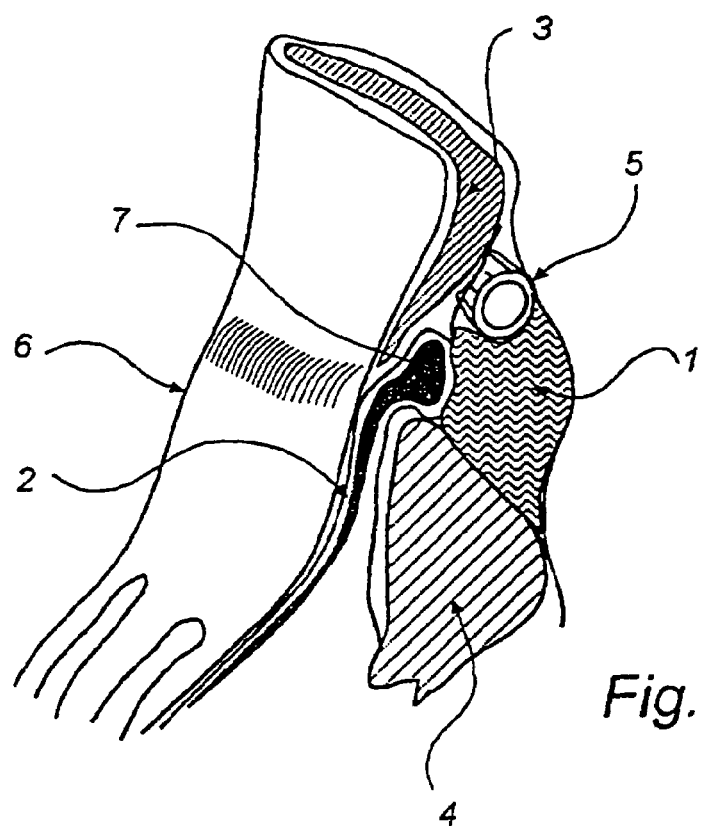

| | | | |
|---|---|---|---|
| 5,163,955 A | 11/1992 | Love et al. | |
| 5,170,802 A | 12/1992 | Mehra | |
| 5,209,730 A | 5/1993 | Sullivan | |
| 5,224,491 A | 7/1993 | Mehra | |
| 5,304,131 A | 4/1994 | Paskar | |
| 5,382,259 A | 1/1995 | Phelps et al. | |
| 5,383,892 A | 1/1995 | Cardon et al. | |
| 5,390,661 A | 2/1995 | Griffith et al. | |
| 5,441,515 A | 8/1995 | Khosravi et al. | |
| 5,449,373 A | 9/1995 | Pinchasik et al. | |
| 5,476,471 A | 12/1995 | Shifrin et al. | |
| 5,496,275 A | 3/1996 | Sirhan et al. | |
| 5,531,779 A | 7/1996 | Dahl et al. | |
| 5,534,007 A | 7/1996 | St. Germain et al. | |
| 5,545,209 A | 8/1996 | Roberts et al. | |
| 5,571,135 A | 11/1996 | Fraser et al. | |
| 5,584,879 A | 12/1996 | Reimold et al. | |
| 5,591,197 A | 1/1997 | Orth et al. | |
| 5,593,442 A | 1/1997 | Klein | |
| 5,607,444 A | 3/1997 | Lam | |
| 5,674,280 A | 10/1997 | Davidson et al. | |
| 5,713,949 A | 2/1998 | Jayaraman | |
| 5,741,274 A | 4/1998 | Lenker et al. | |
| 5,817,126 A | 10/1998 | Imran | |
| 5,824,071 A | 10/1998 | Nelson et al. | |
| 5,876,419 A | 3/1999 | Carpenter et al. | |
| 5,876,433 A | 3/1999 | Lunn | |
| 5,891,108 A | 4/1999 | Leone et al. | |
| 5,911,732 A | 6/1999 | Hojeibane | |
| 5,919,233 A | 7/1999 | Knopf et al. | |
| 5,935,081 A | 8/1999 | Kadhiresan | |
| 5,954,761 A | 9/1999 | Machek et al. | |
| 5,961,545 A | 10/1999 | Lentz et al. | |
| 5,980,552 A | 11/1999 | Pinchasik et al. | |
| 6,006,122 A | 12/1999 | Smits | |
| 6,013,854 A | 1/2000 | Moriuchi | |
| 6,019,739 A | 2/2000 | Rhee et al. | |
| 6,027,516 A * | 2/2000 | Kolobow et al. | 623/1.11 |
| 6,027,525 A | 2/2000 | Suh et al. | |
| 6,051,020 A | 4/2000 | Goicoechea et al. | |
| 6,077,296 A | 6/2000 | Shokoohi et al. | |
| 6,093,203 A | 7/2000 | Uflacker | |
| 6,110,100 A | 8/2000 | Talpade | |
| 6,123,699 A | 9/2000 | Webster, Jr. | |
| 6,161,029 A | 12/2000 | Spreigl et al. | |
| 6,161,543 A | 12/2000 | Cox et al. | |
| 6,165,169 A | 12/2000 | Panescu et al. | |
| 6,168,619 B1 | 1/2001 | Dinh et al. | |
| 6,171,329 B1 | 1/2001 | Shaw et al. | |
| 6,183,411 B1 | 2/2001 | Mortier et al. | |
| 6,203,556 B1 | 3/2001 | Evans et al. | |
| 6,210,432 B1 | 4/2001 | Solem et al. | |
| 6,221,103 B1 | 4/2001 | Melvin | |
| 6,248,119 B1 | 6/2001 | Solem | |
| 6,250,308 B1 | 6/2001 | Cox | |
| 6,264,602 B1 | 7/2001 | Mortier et al. | |
| 6,264,691 B1 | 7/2001 | Gabbay | |
| 6,325,826 B1 | 12/2001 | Vardi et al. | |
| 6,343,605 B1 | 2/2002 | Lafontaine | |
| 6,350,277 B1 | 2/2002 | Kocur | |
| 6,368,348 B1 | 4/2002 | Gabbay | |
| 6,402,679 B1 | 6/2002 | Mortier et al. | |
| 6,402,680 B2 | 6/2002 | Mortier et al. | |
| 6,402,781 B1 | 6/2002 | Langberg et al. | |
| 6,409,760 B1 | 6/2002 | Melvin | |
| 6,537,314 B2 | 3/2003 | Langberg et al. | |
| 6,569,198 B1 | 5/2003 | Wilson et al. | |
| 6,626,899 B2 | 9/2003 | Houser et al. | |
| 6,629,534 B1 | 10/2003 | St. Goar et al. | |
| 6,656,221 B2 | 12/2003 | Taylor et al. | |
| 6,669,687 B1 | 12/2003 | Saadat | |
| 6,706,065 B2 | 3/2004 | Langberg et al. | |
| 6,709,456 B2 | 3/2004 | Langberg et al. | |
| 6,790,231 B2 | 9/2004 | Liddicoat et al. | |
| 6,810,882 B2 | 11/2004 | Langberg et al. | |
| 6,824,562 B2 | 11/2004 | Mathis et al. | |
| 6,989,028 B2 | 1/2006 | Lashinski et al. | |
| 6,997,951 B2 | 2/2006 | Solem et al. | |
| 7,011,682 B2 | 3/2006 | Lashinski et al. | |
| 7,090,695 B2 | 8/2006 | Solem et al. | |
| 2001/0018611 A1 | 8/2001 | Solem et al. | |
| 2001/0044568 A1 | 11/2001 | Langberg et al. | |
| 2002/0016628 A1 | 2/2002 | Langberg et al. | |
| 2002/0019660 A1 | 2/2002 | Gianotti et al. | |
| 2002/0022880 A1 | 2/2002 | Melvin | |
| 2002/0087173 A1 | 7/2002 | Alferness et al. | |
| 2002/0103533 A1 | 8/2002 | Langberg et al. | |
| 2002/0111533 A1 | 8/2002 | Melvin | |
| 2002/0111647 A1 | 8/2002 | Khairkhahan et al. | |
| 2002/0124857 A1 | 9/2002 | Schroeppel | |
| 2002/0151961 A1 | 10/2002 | Lashinski et al. | |
| 2004/0102840 A1 | 5/2004 | Solem et al. | |
| 2004/0102841 A1 | 5/2004 | Langberg et al. | |
| 2004/0133192 A1 | 7/2004 | Houser et al. | |
| 2004/0153146 A1 | 8/2004 | Lashinski et al. | |
| 2004/0176840 A1 | 9/2004 | Langberg et al. | |
| 2005/0060030 A1 | 3/2005 | Lashinski et al. | |
| 2006/0116756 A1 | 6/2006 | Solem et al. | |
| 2006/0116757 A1 | 6/2006 | Lashinski et al. | |

FOREIGN PATENT DOCUMENTS

| | | |
|---|---|---|
| WO | WO 95/16407 | 6/1995 |
| WO | WO 96/34211 | 10/1996 |
| WO | WO 96/40356 | 12/1996 |
| WO | WO 98/18411 | 5/1998 |
| WO | WO 98/51365 | 11/1998 |
| WO | WO 99/44534 | 9/1999 |
| WO | WO 99/53977 | 10/1999 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |

OTHER PUBLICATIONS

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in dentistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2):101-4, one sheet.

Kuo et al., *The use of nickel-titanium alloy in orthopedic surgery in China*, PubMed, Excerpt from Orthopedics Jan. 1989; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/7906notw1.html, News of the Week Materials, Feb. 5, 2001, vol. 79, No. 6, Cenear 79 6 pp. 5, ISSN 0009-2347, three sheets.

Stikeman, *Total Recall*, An MIT Enterprise Technology Review—Innovation, Jun. 2001, two sheets.

European Patent Office Office action dated Dec. 22, 2003 for Application No. 00 946 661.6-2310, 4 sheets.

Written Opinion dated Nov. 8, 2002 for International application No. PCT/EP01/10371, 14 sheets.

International Search Report dated Apr. 23, 2002 for International application No. PCT/EP 01/10371, 4 sheets.

International Search Report dated Mar. 15, 2000 for National application No. SE 9902455-6, 3 sheets.

International Search Report dated Oct. 9, 2002 for National application No. SE 0200073-5, 5 sheets.

International Search Report dated Jun. 5, 2003 for International application No. PCT/EP 02/14655, 7 sheets.

Buchanan et al., Circumferential Suture of the Mitral Annulus for Correction of Mitral Regurgitation in Dogs, Veterinary Surgery, 27: 182-193, 1998.

Buchanan JW, Sammarco CD, Circumferential Suture of the Mitral Annulus for Correction of Mitral Regurgitation in Dogs, PubMed, Excerpt from Vet Surg May-Jun. 1998; 27(3): 182-93, abstract, one sheet.

\* cited by examiner

DEVICE AND METHOD FOR TREATMENT OF MITRAL INSUFFICIENCY

CROSS-REFERENCE TO RELATED APPLICATIONS

This application is a continuation of U.S. patent application Ser. No. 10/019,563, filed Jul. 1, 2002 now U.S. Pat. No. 7,044,967, which is a national stage under 35 U.S.C. 371 of international application PCT/SE00/01369, filed Jun. 28, 2000 which designated the United States, and which international application was published under PCT Article 21(2) in the English language and which claims priority to SE 9902455-6, filed Jun. 29, 1999, the disclosures of which are incorporated fully herein by reference.

The present invention generally relates to a device and a method for treatment of mitral insufficiency and, more specifically, for treatment of dilatation of the mitral annulus.

Mitral insufficiency can result from several causes, such as ischemic disease, degenerative disease of the mitral apparatus, rheumatic fever, endocarditis, congenital heart disease and cardiomyopathy. The four major structural components of the mitral valve are the annulus, the two leaflets, the chordae and the papillary muscles. Any one or all of these in different combinations may be injured and create insufficiency. Annular dilatation is a major component in the pathology of mitral insufficiency regardless of cause. Moreover, many patients have a mitral insufficiency primarily or only due to posterior annular dilatation, since the annulus of the anterior leaflet does not dilatate because it is anchored to the fibrous skeleton of the base of the heart.

Studies of the natural history of mitral insufficiency have found that totally asymptomatic patients with severe mitral insufficiency usually progress to severe disability within five years. At present the treatment consists of either mitral valve replacements or repair, both methods requiring open heart surgery. Replacement can be performed with either mechanical or biological valves.

The mechanical valve carries the risk of thromboembolism and requires anticoagulation, with all its potential hazards, whereas biological prostheses suffer from limited durability. Another hazard with replacement is the risk of endocarditis. These risks and other valve related complications are greatly diminished with valve repair.

Mitral valve repair is theoretically possible if an essentially normal anterior leaflet is present. The basic four techniques of repair include the use of an annuloplasty ring, quadrangular segmental resection of diseased posterior leaflet, shortening of elongated chordae, and transposition of posterior leaflet chordae to the anterior leaflet.

Annuloplasty rings are needed to achieve a durable reduction of the annular dilatation. All the common rings are sutured along the posterior mitral leaflet adjacent to the mitral annulus in the left atrium. The Duran ring encircles the valve completely, whereas the others are open towards the anterior leaflet. The ring can either be rigid, like the original Carpentier ring, or flexible but; non-elastic, like the Duran ring or the Cosgrove-Edwards ring.

Effective treatment of mitral insufficiency currently requires open-heart surgery, by the use of total cardiopulmonary by-pass, aortic cross-clamping and cardioplegic arrest.

To certain groups of patient, this is particular hazardous. Elderly patients, patients with a poor left ventricular function, renal disease, severe calcification of the aorta, previous cardiac surgery or other concomitant diseases, would in particular most likely benefit from a less invasive approach, even if repair is not complete. The current trend towards less invasive coronary artery surgery, without cardiopulmonary by-pass, as well as PTCA will also call for a development of a less invasive method for repair of the often concomitant mitral insufficiency.

Therefore, a first object of the present invention is to provide a device and a method for treatment of mitral insufficiency without the need for cardiopulmonary by-pass and opening of the chest and heart.

A second object of the invention is to provide reduction of the mitral annulus using less invasive surgery.

These and other objects are attained by a device as defined in the appended claim 1, and by a method as defined in the appended claim 7.

According to the present invention, a device for treatment of mitralis insufficiency comprises an elongate body having such dimensions as to be insertable into the coronary sinus and having two states, in a first state of which the elongate body has a shape that is adaptable to the shape of the coronary sinus, and to the second state of which the elongate body is transferable from the said first state assuming a reduced radius of curvature, whereby the radius of curvature of the coronary sinus is reduced as well as the circumference of the mitral valve annulus, when the elongate body is positioned in the coronary sinus.

Preferably, means are provided for the transfer of the elongate body to the second state by bending and/or shortening it from a larger radius of curvature to a smaller radius of curvature.

The transfer means may comprise means for bending and/or shortening the elongate body by a preferably asymmetric contraction thereof.

Further, the elongate body may comprise a memory material providing the transfer to the second state.

In a preferred embodiment, the elongate body may comprise a stent. In an alternative embodiment, the device according to the invention may comprise several stent sections and said bending and/or shortening means may comprise wires for shortening the distance between the stent sections.

According to a second aspect, a method of reducing the circumference of the mitral valve annulus comprises the steps of inserting an elongate body into the coronary sinus in the vicinity of the posterior leaflet of the mitral valve, and then providing a bending and/or shortening of the elongate body when positioned in the coronary sinus so as to reduce the curvature of the coronary sinus and thereby reduce the circumference of the mitral valve annulus.

Thus, the present invention takes advantage of the position of the coronary sinus being close to the mitral annulus. This makes repair possible by the use of current catheter-guided techniques.

The coronary veins drain blood from the myocardium to the right atrium. The smaller veins drain blood directly into the atrial cavity, and the larger veins accompany the major arteries and run into the coronary sinus which substantially encircles the mitral orifice and annulus. It runs in the posterior atrioventricular groove, lying in the fatty tissue between the left atrial wall and the ventricular myocardium, before draining into the right atrium between the atrial septum and the post-Eustachian sinus.

In an adult, the course of the coronary sinus may approach within 5-15 mm of the medial attachment of the posterior leaflet of the mitral valve. Preliminary measurements performed at autopsies of adults of normal weight show similar results, with a distance of 5.3±0.6 mm at the medial attachment and about 10 mm at the lateral aspect of the posterior leaflet. The circumference of the coronary sinus was 18.3±2.9 mm at its ostium (giving a diameter of the posterior leaflet of 5.8±0.9 mm) and 9.7±0.6 mm along the lateral aspect of the posterior leaflet (corresponding to a diameter of 3.1±0.2 mm).

Figure 2:
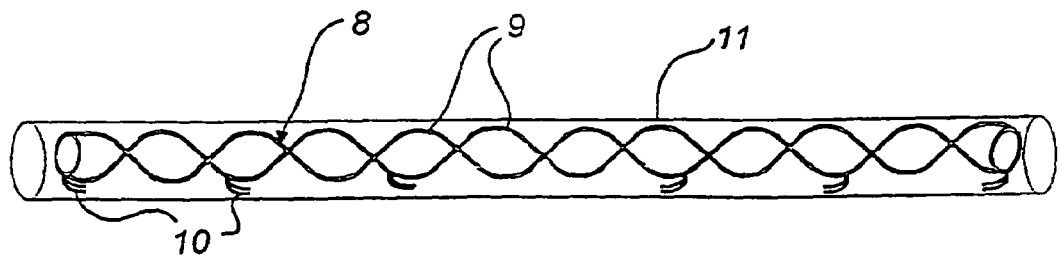
Figure 3:
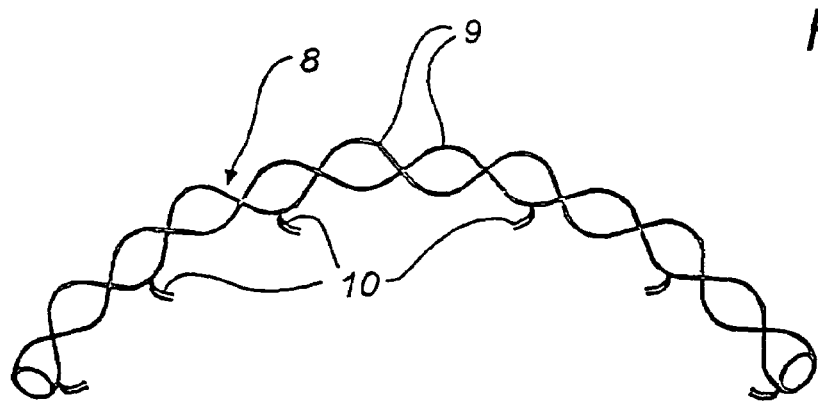
Figure 4:
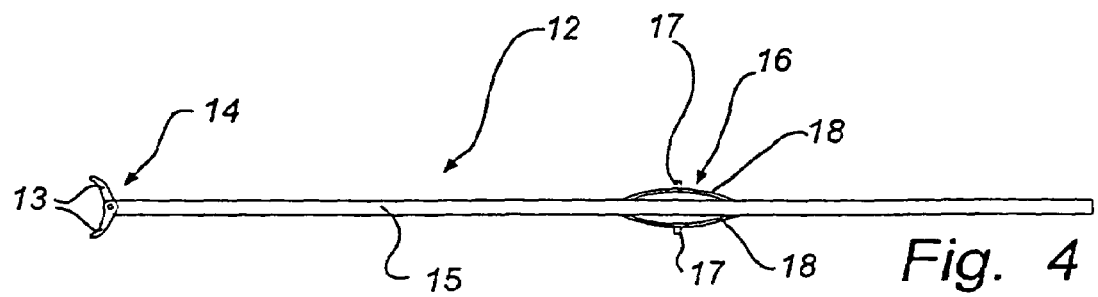
Figure 5:
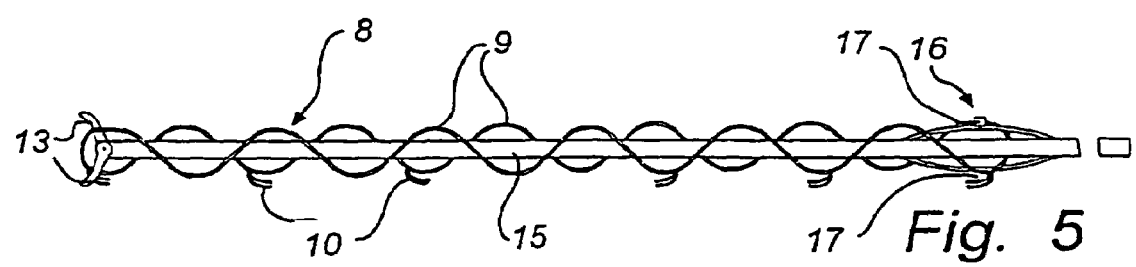
Figure 6:
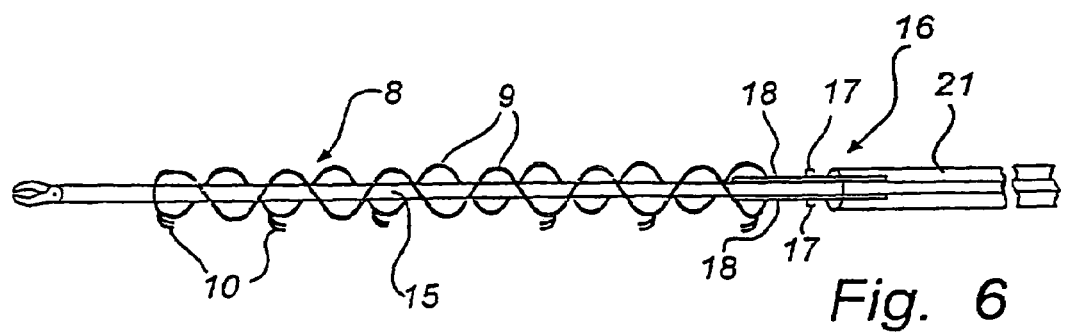
Figure 7:
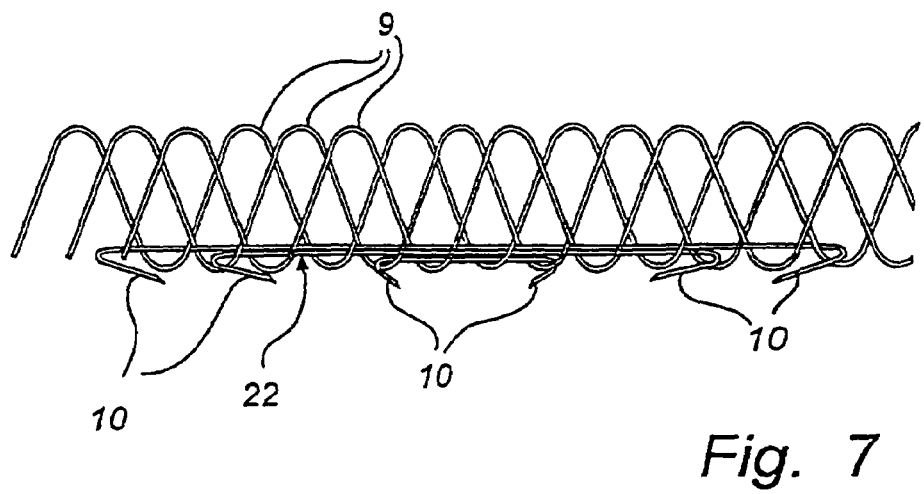

The invention will be better understood by the following description of preferred embodiments referring to the appended drawings, in which FIG. 1 is a cross-sectional view of a part of a heart, FIGS. 2 and 3 are schematic views of a first embodiment of a device according to the present invention, FIGS. 4-6 are schematic views illustrating an instrument, which may be used when positioning the device shown in FIGS. 2 and 3 in the coronary sinus, FIG. 7 is a partial, enlarged view of the first embodiment shown in FIG. 2.

Figure 8:
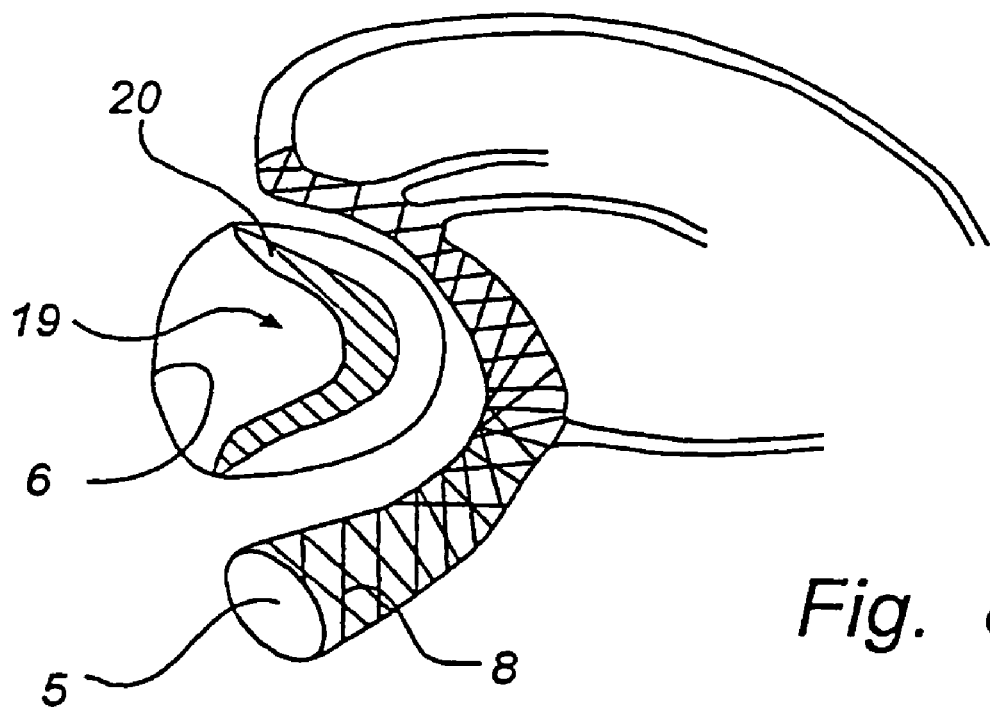
Figure 9:
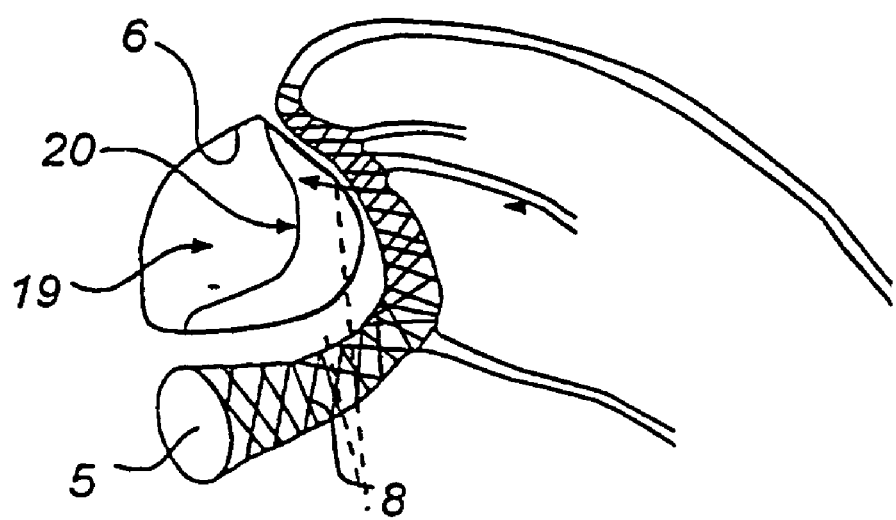
Figure 10:
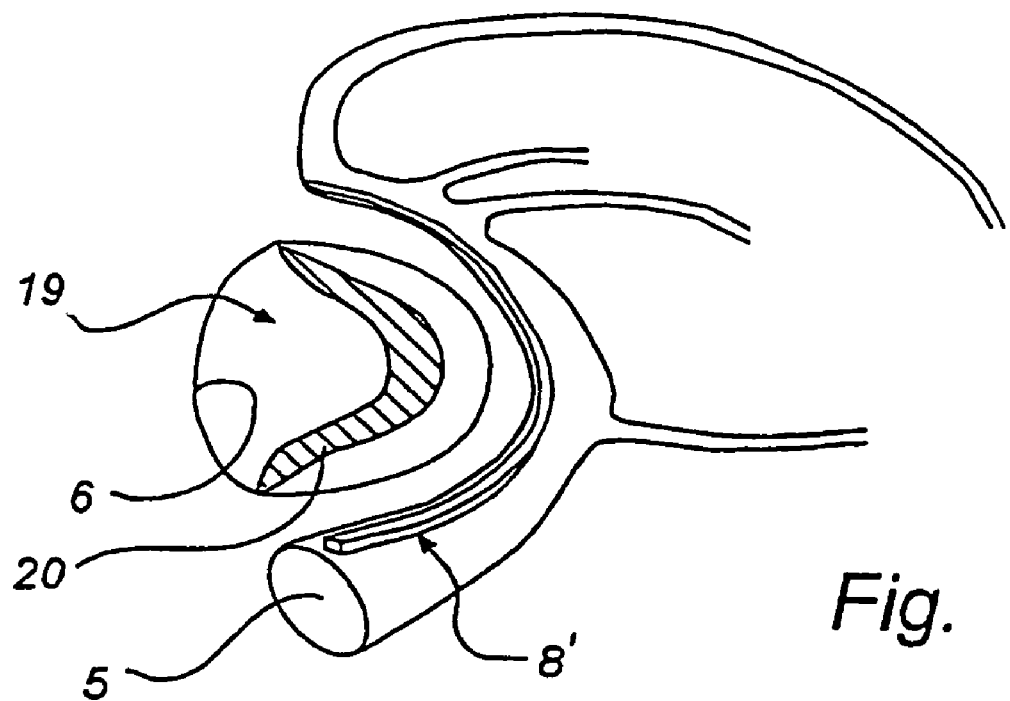
Figure 11:
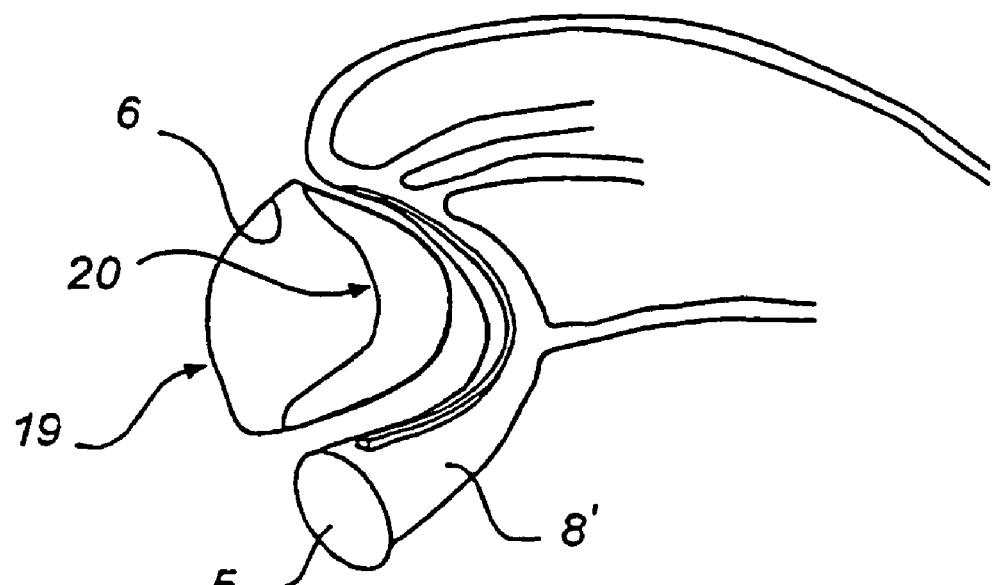
Figure 12:
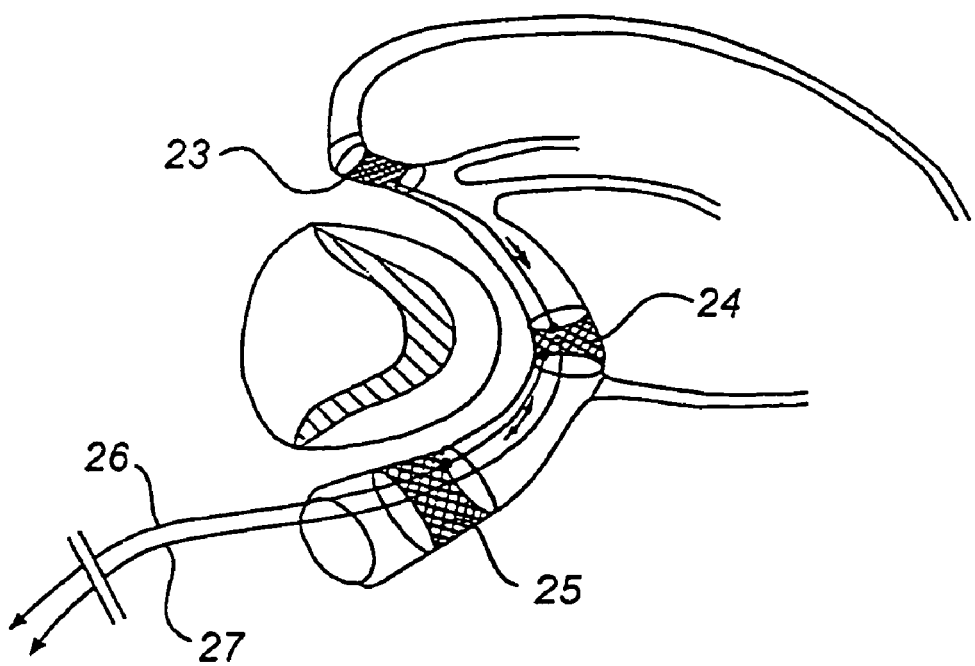
Figure 13:
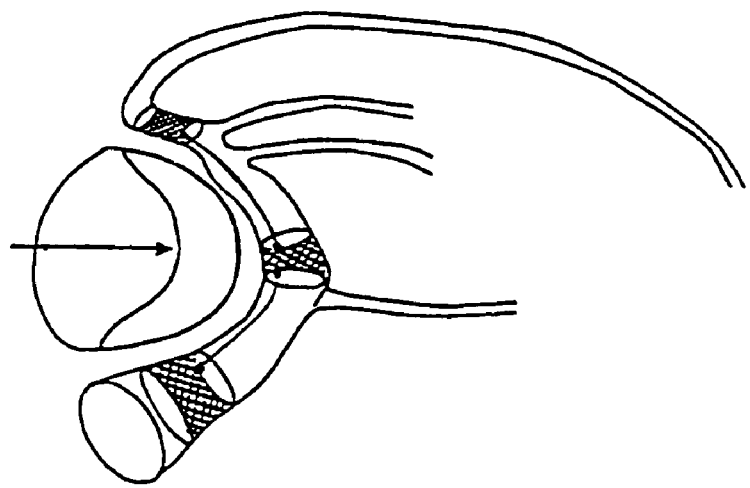

FIGS. 8 and 9 are schematic views illustrating the positioning of the device of FIGS. 2 and 3 in the coronary sinus, FIGS. 10 and 11 are schematic views illustrating the positioning of a second embodiment of the device according to the present invention in the coronary sinus, and FIGS. 12 and 13 are schematic views illustrating the positioning of a third embodiment of the device according to the present invention in the coronary sinus.

FIG. 1 is a cross-sectional view through the heart area of the posterior atrioventricular groove 1, which is filled with fatty tissue. It shows the posterior leaflet 2 of the mitral valve and the adjoining parts 3, 4 of the atrial myocardium and the ventricular myocardium. The coronary sinus 5 is shown close to the mitral annulus 6 and behind the attachment 7 of the posterior leaflet 2. Since the coronary sinus 5 substantially encircles the mitral annulus 6, a reduction of the radius of curvature of the bent coronary sinus 5 also will result in a diameter and circumference reduction of the mitral annulus 6.

The device of FIG. 2 comprises an elongate body 8 made of memory metal, e.g. Nitinol, or other similar material which has a memory of an original shape, illustrated in FIG. 3, and can be temporary forced into another shape, illustrated in FIG. 2. This elongate body 8 comprises one, two or more memory metal strings 9 of helical or other shape so as to fit together and be able of permitting the movements described below. Along the elongate body 8 several hooks 10 are fastened so as to extend radially out therefrom. These hooks 10 are covered by a cover sheet 11 in FIG. 2.

The elongate body 8 is forced into a stretched or extended state by means of a stabilising instrument 12 shown in FIG. 4. This instrument 12 has two arms 13 at a distal end 14 of a rod is and a locking means 16 at a proximal end of the rod 15. The distance between the ends of the rod 15 corresponds to the desired length of the elongate body 8 when being inserted into the coronary sinus 5.

The arms 13 are free to move between the position shown in FIG. 4 and a position in alignment with the rod 15, as shown in FIG. 6. The locking means 16 has two locking knobs 17, which are pressed radially outwards from the rod 15 by two spring blades 18. Thus, the elongated body 8 can be pushed over the rod 15 of the stabilising instrument 12, then stretched between the arms 13 and the knobs 17, and finally locked in its stretched state on the stabilising instrument 12 between the arms 13 and the knobs 17, as illustrated in FIG. 5.

The rod 15 may be a metal wire which is relatively stiff between the distal end 14 and the locking means 16 but still so bendable that it will follow the shape of the coronary sinus 5. Proximally of the locking means 16 the metal wire of the stabilising instrument 11 is more pliable to be able to easily follow the bends of the veins.

The above-described elongate body 8 is positioned in the coronary sinus 5 in the following way:

An introduction sheet (not shown) of synthetic material may be used to get access to the venous system. Having reached access to the venous system, a long guiding wire (not shown) of metal is advanced through the introduction sheet and via the venous system to the coronary sinus 5. This guiding wire is provided with X-ray distance markers so that the position of the guiding wire in the coronary sinus 5 may be monitored.

The elongate body 8 is locked onto the stabilising instrument 12, as shown in FIG. 5, and introduced into the long cover sheet 11 of synthetic material. This aggregate is then pushed through the introduction sheet and the venous system to the coronary sinus 5 riding on the guiding wire. After exact positioning of the elongate body 8 in the coronary sinus 5, as illustrated in FIG. 8 where the mitral valve 19 is shown having a central gap 20, the cover sheet 11 is retracted exposing the elongate body 8 within the coronary sinus 5. This manoeuvre allows the hooks 10 on the elongate body 8 to dig into the walls of the coronary sinus 5 and into the heart. The elongate body 8 is still locked on to the stabilising instrument 12 such that the hooks 10 engage the walls of the coronary sinus 5 in the stretched or extended state of the elongate body 8.

A catheter 21, shown in FIG. 6, is pushed forward on the guiding wire and the rod 15 for releasing the elongate body 8 from the locking means 16 by pressing the spring blades 18 towards the rod 15. This movement releases the knobs 17 as well as the arms 13 from engagement with the elongate body 8 which contracts as illustrated in FIG. 9 and as a result bends towards the mitral valve annulus 6 moving the posterior part thereof forward (shown by arrows in FIG. 9). This movement reduces the circumference of the mitral valve annulus 6 and thereby closes the central gap 20.

FIG. 7 illustrates a part of an arrangement of the wires 9 and the hooks 10 along a peripheral part of the elongate body 8, whereby the elongate body 8 will be asymmetrically contracted resulting in a bending thereof when interconnecting parts 22 of at least some of the hooks 10 are shortened to an original shape.

FIGS. 10 and 11 illustrate an alternative embodiment of an elongate body 8', which is a solid wire in the shape of an open U-shaped ring that will engage the wall of the coronary sinus 5 most adjacent to the mitral valve annulus 6 when inserted into the coronary sinus 5. The elongate body 8' consists of a memory metal material which when reverting to its original shape will bend as illustrated in FIG. 11. The return of the open ring 8' to its original shape may be initiated in several ways, as is obvious to the man skilled in the art.

The third embodiment of the elongate body 8", illustrated in FIGS. 12 and 13, comprises three stent sections 23-25 positioned at one end of the elongate body 8", at the middle thereof and at the other end of the elongate body 8", respectively. These stent sections 23-25 may be positioned in the coronary sinus 5 as illustrated by conventional means, such that their positions are fixed. They are connected by wires 26, 27, which may be manoeuvred from outside the vein system such that the distances between the adjacent stent sections 23, 24 and 24, 25 are reduced. More specifically, these distances are reduced asymmetrically, i.e. more on the side of coronary sinus 5 most adjacent to the posterior part of the mitral valve annulus 6. Thereby, the elongate body 8" is bent, as illustrated in FIG. 13, and presses the coronary sinus 5 against the mitral valve annulus 6 closing the gap 20.

Concludingly, the present invention provides a device placed in the coronary sinus, designed to reduce the dilatation of the mitral annulus. This device is at a distance from the attachment of the posterior leaflet that does not much exceed the distance at which present annuloplasty rings are placed by open surgery techniques, and the coronary sinus is along its entire course large enough to hold such a device. The device could be positioned by catheter technique or any other adequate technique and offers a safer alternative to the current open surgery methods. The device could be designed or heparincoated so as to avoid thrombosis in the coronary sinus, thus reducing the need for aspirin, ticlopedine or anticoagulant therapy.

It is to be understood that modifications of the above-described device and method can be made by people skilled in the art without departing from the spirit and scope of the invention.

The invention claimed is:

1. A device for treating tissue near a valve to modify flow through the valve, comprising:
    an elongate body having a central region and at least two anchoring regions on opposing end portions of the central region, wherein each anchoring region is configured to be anchored to opposing areas of tissue against or adjacent to an annulus of the valve and urge the areas of tissue towards one another; and
    the elongate body being further configured for delivery through a catheter to the tissue whereby the elongate body has a first shape during the delivery and a second shape after the delivery.

2. The device of claim 1 wherein the central region comprises a continuous alternating length.

3. The device of claim 1 wherein each of the anchoring regions comprise a fastener.

4. The device of claim 1 the elongate body being interwoven such that a plurality of spaces are defined therebetween in the second shape.

5. The device of claim 1 further comprising a biocompatible fastener for attaching each of the anchoring regions to the tissue.

6. The device of claim 5 wherein the biocompatible fastener comprises a distal end and a proximal end, the proximal end defining a projection for securing the anchoring region, and the distal end being configured for attachment to the tissue.

7. The device of claim 1 wherein the elongate body is configured to approximate a portion of periphery defined by the valve, the central region comprising an accurate length whereby each of the anchoring regions is in apposition to each other.

8. The device of claim 7 wherein the portion of the periphery approximated by the elongate body comprises at least about 50%.

9. The device of claim 7 wherein each of the anchoring regions is biased towards the central region.

10. The device of claim 1 wherein the elongate body comprises Nickel-Titanium alloy.

11. The device of claim 1 wherein the elongate body is at least partially coated with a coating layer.

12. The device of claim 1 wherein the catheter comprises an elongate tubular member having a distal end and a proximal end with a lumen therebetween, the distal end defining a delivery port configured to pass the elongate body therethrough.

13. The device of claim 12 wherein the catheter further comprises a stylet having a distal end and a proximal end with a length therebetween, the stylet being slidingly disposed in the lumen and being manipulatable from its proximal end.

14. The device of claim 13 wherein the stylet distal end is angled.

15. The device of claim 13 wherein the catheter further comprises a linear advancement mechanism connected to the proximal end of the stylet.

16. A method for treating tissue near a valve to modify flow through the valve, comprising:
    providing an elongate body having a central region, a first anchoring region, and a second anchoring region, each of the anchoring regions being attached to opposing end portions of the central region;
    placing a delivery catheter near the tissue;
    urging the elongate body through a distal opening defined in the catheter such that the first anchoring region exits the distal opening and attaches to a first area of the tissue against or adjacent to an annulus of the valve; and
    further urging the elongate body through the distal opening such that the second anchoring region exits the distal opening and attaches to a second area of the tissue against or adjacent to the annulus of the valve such that the first area and the second area are urged towards one another by the elongate body.

17. The method of claim 16 further comprising providing a biocompatible fastener for attaching the first and the second anchoring regions to the first and the second areas of tissue.

18. The method of claim 16 wherein the elongate body is comprised of a shape memory alloy.

19. The method of claim 18 wherein the shape memory alloy comprises Nickel-Titanium alloy.

20. The method of claim 16 wherein the first anchoring region forms a shape configured for attachment to the first area of the tissue upon exiting the distal opening.

21. The method of claim 16 wherein the second anchoring region forms a shape configured for attachment to the second area of the tissue upon exiting the distal opening.

22. The method of claim 16 wherein the first area and the second area are located about 180° apart.

23. The method of claim 16 wherein urging the elongate body through the distal opening defined in the catheter comprises advancing a stylet having a distal end and a proximal end with a length therebetween through the delivery catheter to urge the elongate body.

24. The method of claim 23 wherein the stylet distal end is angled.

25. The method of claim 23 wherein the stylet is advanced by a linear advancement mechanism connected at the proximal end of the stylet.

* * * * *